United States Patent
Jagger et al.

(10) Patent No.: US 9,060,836 B2
(45) Date of Patent: Jun. 23, 2015

(54) PATTERNED IMPLANT AND METHOD

(75) Inventors: Karl A. Jagger, Deephaven, MN (US); Dean W. Hacker, Maple Grove, MN (US); Jessica E. Felton, Minneapolis, MN (US); John R. Frigstad, St. Anthony, MN (US); Alex A. Peterson, Maple Grove, MN (US)

(73) Assignee: AMS Research Corporation, Minnetonka, MN (US)

( * ) Notice: Subject to any disclaimer, the term of this patent is extended or adjusted under 35 U.S.C. 154(b) by 479 days.

(21) Appl. No.: 12/953,268

(22) Filed: Nov. 23, 2010

(65) Prior Publication Data
US 2011/0144417 A1    Jun. 16, 2011

Related U.S. Application Data

(60) Provisional application No. 61/263,557, filed on Nov. 23, 2009.

(51) Int. Cl.
*A61F 2/00* (2006.01)

(52) U.S. Cl.
CPC ............ *A61F 2/0045* (2013.01); *A61F 2/0063* (2013.01); *A61F 2002/0068* (2013.01); *A61F 2002/0081* (2013.01)

(58) Field of Classification Search
CPC ... A61F 2/0004; A61F 2/0031; A61F 2/0036; A61F 2/0045; A61F 2/0063; A61F 2/0077; A61F 2002/0068; A61F 2002/0081
USPC ................ 600/29–32, 37; 606/151, 157, 153
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,384,073 A | 5/1968 | Van Winkle, Jr. |
| 3,789,828 A | 2/1974 | Schulte |
| 4,548,202 A | 10/1985 | Duncan |
| 4,775,380 A | 10/1988 | Seedhom et al. |
| 4,865,031 A | 9/1989 | O'Keeffe |
| 5,032,508 A | 7/1991 | Naughton et al. |

(Continued)

FOREIGN PATENT DOCUMENTS

| | | |
|---|---|---|
| EP | 1060714 A3 | 9/2002 |
| IT | 1299162 | 4/1998 |

(Continued)

OTHER PUBLICATIONS

Moir, J. Chassar et.al., The Gauze-Hammock Operation, The Journal of Obstetrics and Gynaecology of British Commonwealth, vol. 75 No. 1, pp. 1-9 (Jan. 1968).

(Continued)

*Primary Examiner* — Charles A Marmor, II
*Assistant Examiner* — Carrie R Dorina
(74) *Attorney, Agent, or Firm* — Gregory L. Koeller

(57) ABSTRACT

A unitary or homogeneous patterned implant is provided. The implant is constructed of patterned cells formed by way of a molding, die casting, laser etching, laser cutting, extruding, and the like. Portions of the implant can be formed into sinusoid or other waveform strut members to control and promote elongation, expansion or contraction along single or multiple axes. As such, controlled and designated stress, tension and compression distribution is promoted across specific or localized areas of the implant.

20 Claims, 13 Drawing Sheets

(56) References Cited

U.S. PATENT DOCUMENTS

| | | |
|---|---|---|
| 5,919,232 A | 7/1999 | Chaffringeon et al. |
| 6,010,447 A | 1/2000 | Kardjian |
| 6,031,148 A | 2/2000 | Hayes et al. |
| 6,482,214 B1 | 11/2002 | Sidor, Jr. et al. |
| 6,599,323 B2 | 7/2003 | Melican et al. |
| 6,638,284 B1 | 10/2003 | Rousseau et al. |
| 6,691,711 B2 | 2/2004 | Raz |
| 6,884,212 B2 | 4/2005 | Thierfelder et al. |
| 6,953,428 B2 | 10/2005 | Gellman et al. |
| 7,025,063 B2 | 4/2006 | Snitkin |
| 7,087,065 B2 | 8/2006 | Ulmsten et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,303,525 B2 | 12/2007 | Watschke et al. |
| 7,347,812 B2 | 3/2008 | Mellier |
| 7,351,197 B2 | 4/2008 | Montpetit et al. |
| 7,393,320 B2 | 7/2008 | Montpetit et al. |
| 7,407,480 B2 | 8/2008 | Staskin |
| 7,422,557 B2 | 9/2008 | Arnal |
| 7,500,945 B2 | 3/2009 | Cox |
| 7,513,865 B2 | 4/2009 | Bourne et al. |
| 7,601,118 B2 | 10/2009 | Smith et al. |
| 7,722,527 B2 | 5/2010 | Bouchier et al. |
| 7,722,528 B2 | 5/2010 | Arnal et al. |
| 7,762,969 B2 | 7/2010 | Gellman et al. |
| 2002/0028980 A1 | 3/2002 | Thierfelder et al. |
| 2002/0103542 A1 | 8/2002 | Bilbo |
| 2002/0138025 A1 | 9/2002 | Gellman et al. |
| 2002/0147382 A1 | 10/2002 | Neisz et al. |
| 2002/0151762 A1 | 10/2002 | Rocheleau |
| 2003/0004581 A1 | 1/2003 | Rousseau |
| 2005/0004427 A1 | 1/2005 | Cervigni |
| 2005/0234291 A1* | 10/2005 | Gingras ............... 600/30 |
| 2005/0240076 A1* | 10/2005 | Neisz et al. ........... 600/30 |
| 2005/0277806 A1 | 12/2005 | Cristalli |
| 2006/0058578 A1* | 3/2006 | Browning ............. 600/37 |
| 2006/0205995 A1* | 9/2006 | Browning ............. 600/29 |
| 2006/0229493 A1 | 10/2006 | Weiser et al. |
| 2006/0229596 A1 | 10/2006 | Weiser et al. |
| 2007/0299300 A1* | 12/2007 | Smith et al. ........... 600/30 |
| 2008/0132754 A1 | 6/2008 | Thierfelder et al. |
| 2010/0261955 A1 | 10/2010 | O'Hern et al. |

FOREIGN PATENT DOCUMENTS

| | | | | |
|---|---|---|---|---|
| WO | WO9317635 A1 | 9/1993 | | |
| WO | WO0057812 A1 | 10/2000 | | |
| WO | WO0106951 A1 | 2/2001 | | |
| WO | WO0156499 A1 | 8/2001 | | |
| WO | WO0222184 A2 | 3/2002 | | |
| WO | WO02091950 A1 | 11/2002 | | |
| WO | WO03028585 A2 | 4/2003 | | |
| WO | WO03037215 A2 | 5/2003 | | |
| WO | WO03041613 A1 | 5/2003 | | |
| WO | WO03096929 A1 | 11/2003 | | |
| WO | WO2004045457 A1 | 6/2004 | | |
| WO | WO2005094741 A1 | 10/2005 | | |
| WO | WO2007/070141 | * | 6/2007 | ............... A61F 2/00 |
| WO | WO2007097994 | | 8/2007 | |
| WO | WO2008057261 A2 | 5/2008 | | |
| WO | WO2009/017680 | * | 5/2009 | ............. A61B 17/04 |

OTHER PUBLICATIONS

Nichols, David H., The Mersilene Mesh Gauze-Hammock for Severe Urinary Stress Incontinence, Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Richardson, David A. et al., Delayed Reaction to the Dacron Buttress Used In Urethropexy, The Journal of Reproductive Medicine, pp. 689-692, vol. 29, No. 9 (Sep. 1984).

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).

Sullivan, Eugene S. et al., Total Pelvic Mesh Repair a Ten-Year Experience, Dis. Colon Rectum, vol. 44, No. 6, pp. 857-863 (Jun. 2001).

Visco, Anthony G. et al., Vaginal Mesh Erosion After Abdominal Sacral Colpopexy, Am J Obstet Gynecol, vol. 184, n. 3, pp. 297-302 (297-302).

Pourdeyhimi, B. Porosity of Surgical Mesh Fabrics: New Technology, J. Biomed. Mater. Res.: Applied Biomaterials, vol. 23, No. A1. pp. 145-152 (1989).

Brochure, "GPS for Pelvic Floor Repair," Gynecare Prolift, 6 pages, 2005.

Advantage A/T™, Surgical Mesh Sling Kit, Boston Scientific, 6 pages (2002).

Cervigni, Mauro et al., The Use of Synthetics in the Treatment of Pelvic Organ Prolapse, Voiding Dysfunction and Female Urology, vol. 11, pp. 429-435 (2001).

Debodinance, Philipp et al., "Tolerance of Synthetic Tissues in Touch With Vaginal Scars: Review to the Point of 287 Cases", European Journal of Obstetrics & Gynecology and Reproductive Biology 87 (1999) pp. 23-30.

Diana, et al., Treatment of Vaginal Vault Prolase With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Flood, C.G. et al., Anterior Colporrhaphy Reinforce With Marlex Mesh for the Treatment of Cystoceles, International Urogynecology Journal, vol. 9, pp. 200-204 (1998).

Gynecare TVT Tension-Free Support for Incontinence, The tension-free solution to female Incontinence, Gynecare Worldwide,6 pages, (2002).

IVS Tunneller—A Universal instrument for anterior and posterior intra-vaginal tape placement, Tyco Healthcare, 4 pages (Aug. 2002).

Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

Lichtenstein, Irving L. et al, The Tension Free Hernioplasty, The American Journal of Surgery, vol. 157 pp. 188-193 (Feb. 1989).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

* cited by examiner

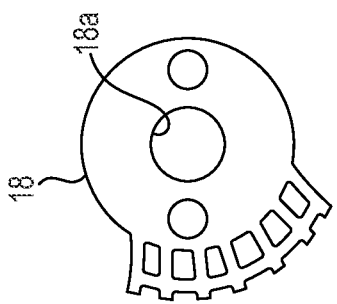
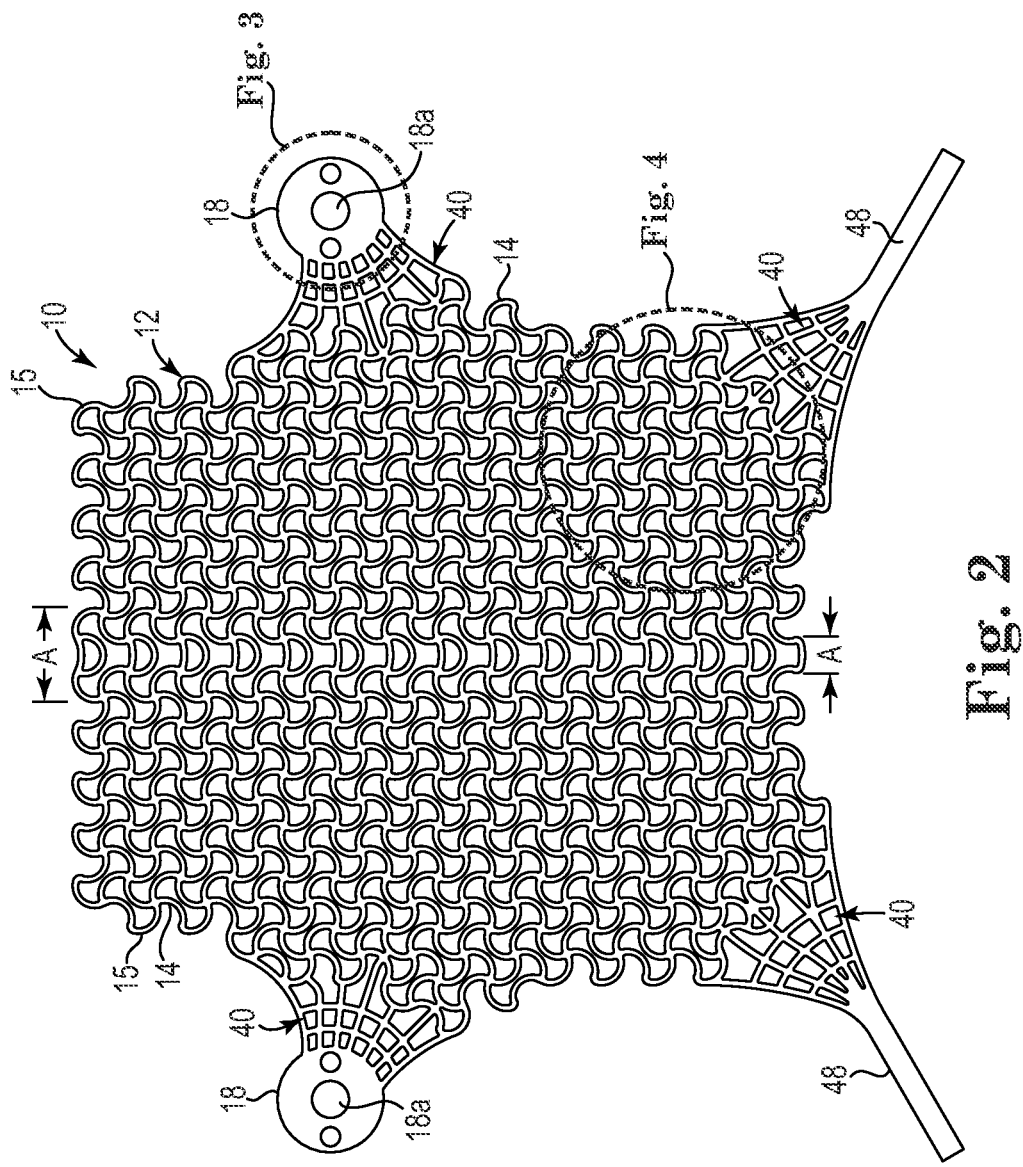

ENTERPRISE 1.5X

PINWHEEL 1.3X

PINWHEEL 1.0X

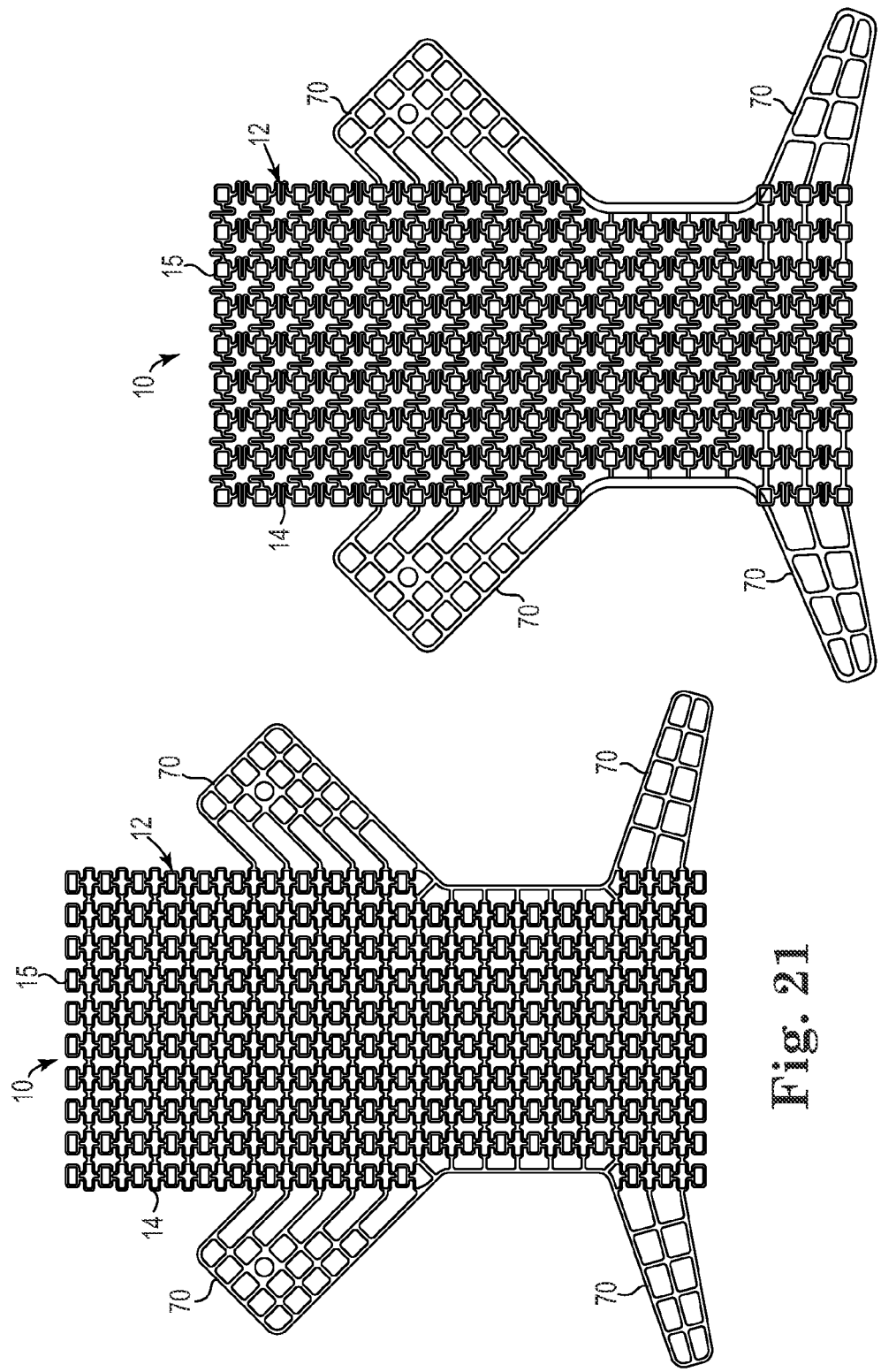

# PATTERNED IMPLANT AND METHOD

PRIORITY

This Application claims priority to and the benefit of U.S. Provisional Application No. 61/263,557, filed Nov. 23, 2009, which is incorporated herein by reference in its entirety.

FIELD OF THE INVENTION

The present invention relates generally to surgical methods and apparatus and, more specifically, to surgically implantable patterned support devices and methods for forming and using the same.

BACKGROUND OF THE INVENTION

Pelvic health for men and women is a medical area of increasing importance, at least in part due to an aging population. Examples of common pelvic ailments include incontinence (fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed. Physical stresses that can cause urinary incontinence include jumping, coughing, sneezing and laughing to name a few.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Many strategies have been implemented over the years to provide mesh implants adapted to enhance therapeutic support of the respective pelvic tissues. For instance, sling and other implant devices are known to provide support of the urethra or bladder neck in treating urinary incontinence in patients. Further, various mesh implants have been adapted to provide pelvic floor support to treat certain prolapse disorders.

Many of the implants promoted for treating incontinence, prolapse and other pelvic disorders were born from and inherited the material and geometric restraints of existing stent and hernia implants. While objectively effective in their respective applications, such stent and hernia implants are naturally constructed to address very different issues. Namely, the requisite barrier, rigidity and tissue integration and compatibility needs of a hernia mesh or vascular stent implant can be very disparate from the implant characteristics required in treating pelvic incontinence and prolapse disorders.

Although these traditional mesh implants have had a tremendous benefit for those suffering from incontinence and prolapse, there is still room for improvement. As a result, there is a desire to obtain a uniquely applicable, minimally invasive and highly effective implantable mesh support that can be used to treat incontinence, organ prolapse and other pelvic disorders and conditions.

SUMMARY OF THE INVENTION

The present invention describes implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle or ligament weakness. Other uses include providing a support or platform for plastic surgery, hernia repair, and ortho repairs and support, to name a few. Embodiments of the implants can include a tissue support portion and one or more extending arms or anchoring portions.

In various embodiments, the implants can be formed of patterned cells by way of a molding, die casting, laser etching, laser cutting, extruding, and the like. Such a pattern cut or formed implant can be constructed of a polymer material to provide a lattice support structure of repeated cells. Unlike woven or knitted conventional implants, the implants of the present invention are a homogeneous unitary construct.

Portions of the implant can be formed into sinusoid or other waveform strut members to control and promote elongation, expansion or contraction along single or multiple axes. As such, controlled and designated stress, tension and compression distribution is promoted across specific or localized areas of the construct. Further, the implant can be formed such that regions or portions can include anchoring features to facilitate engagement and attachment of the implant to target tissue sites. In addition to anchoring to internal tissue, it is also possible to have one or more portions of the implant extend out of an incision or orifice in a patient.

In addition, each patterned cell of the implant can include uniquely shaped or cut strut members configured to define cell voids, to optimize or increase tissue in-growth, to promote load bearing along select portions of the implant, to compensate for stiffness, elongation, compression, and tensile strength. The material and cell construct of the implant can be configured to promote flexibility while still providing optimal implant strength and tissue support. Further, the stable geometrical and dimensional attributes of the implant provide a flexible device that can be easily positioned and deployed while also avoiding undesirable implant warping or bunching.

In addition to molding and laser cutting the struts and other features of the implant, punching, 3-D printing and other methods and techniques can be employed in making the implant. Further, the struts or other portions of the implant can be coated to provide additional control over expansion, compression, and to protect from or promote tissue in-growth.

The implants, or portions thereof, can be adapted to provide desirable adjustability, stress distribution, anchoring, stabilization, variable elongation, and the like.

BRIEF DESCRIPTION OF THE DRAWINGS

FIG. 2 is a front view of a unitary patterned implant in accordance with embodiments of the present invention.

FIG. 3 is a partial close-up view of an eyelet feature for a unitary patterned implant in accordance with embodiments of the present invention.

FIGS. 19-22 are front views of exemplary unitary patterned implants in accordance with embodiments of the present invention.

DETAILED DESCRIPTION OF PREFERRED EMBODIMENTS

Figure 1:
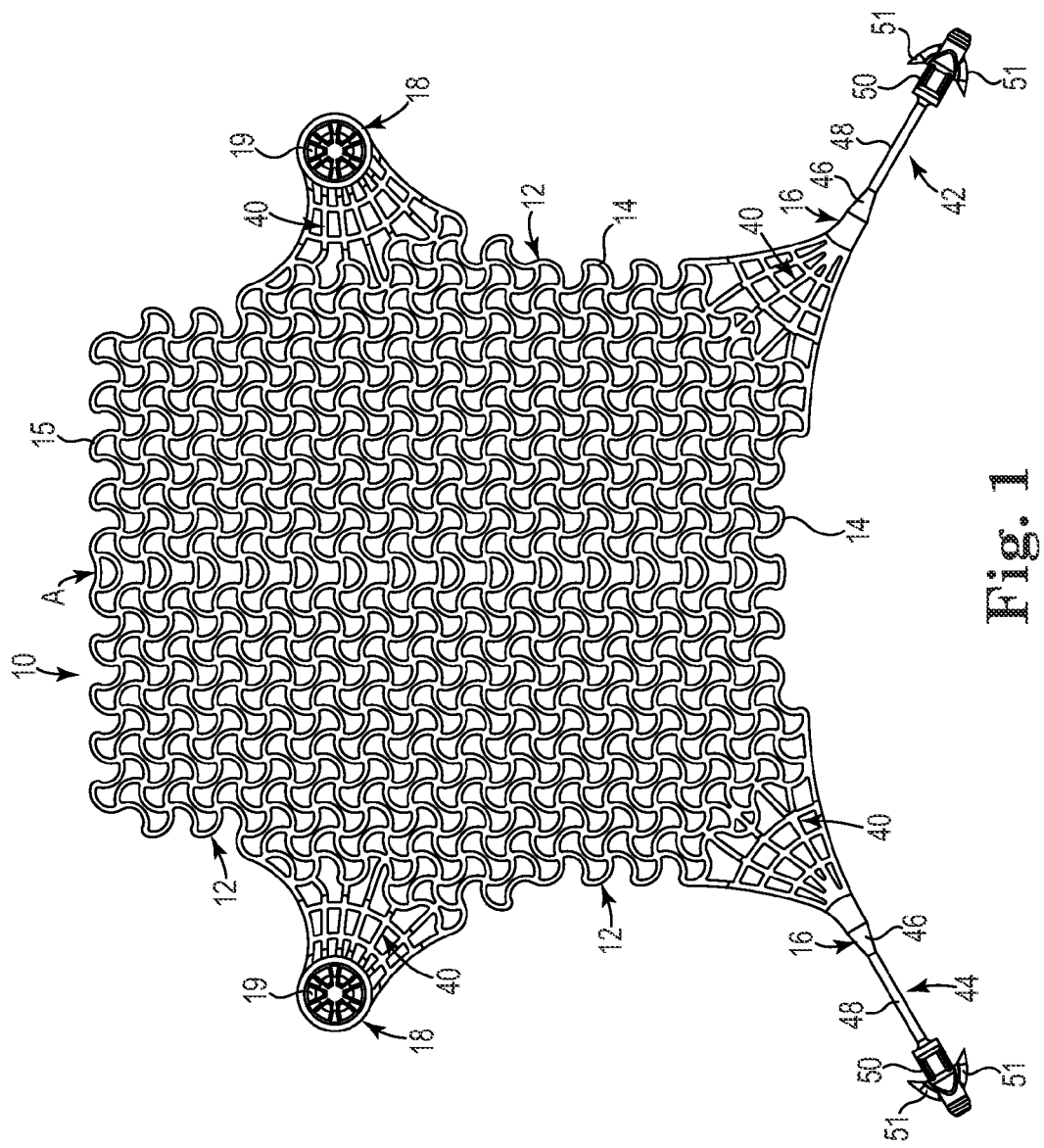
FIG. 1 is a front view of a unitary patterned implant in accordance with embodiments of the present invention.

Referring generally to FIGS. 1-22, various embodiments of a patterned implant 10 and methods are shown. In general, the implants 10 can include at least a support portion 12 and in other embodiments a support portion 12 and anchoring portions 16. Various portions of the implant 10 can be constructed of polymer materials, e.g., into a molded generally planar structure or cut from a thin generally planar film or sheet material. Examples of acceptable polymer materials available in constructing or forming the implant 10 and its components and related systems and kits can include polypropylene, polyethylene, fluoropolymers or like biocompatible materials.

The various implants 10, structures, features and methods detailed herein are envisioned for use with many known implant and repair devices (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2010/0261955, 2002/151762 and 2002/147382. Accordingly, the above-identified disclosures are fully incorporated herein by reference in their entirety.

Referring generally to FIGS. 1-13, various embodiments of the implant 10 are shown. Portions of the implant 10, such as the support portion 12, can be formed or patterned by way of a polymer molding process to create a unitary homogeneous non-woven, or non-knitted, device or construct. Other embodiments can be formed from an already unitary homogeneous sheet or film via laser cutting, die cutting, stamping and like procedures.

As a result of the manufacturing process, molding or cutting, repeating cells form a lattice structure for at least the support portion 12 of the implant 10. Portions of the implant 10 can be formed into sinusoid, or other waveforms or undulating struts 14 to control elongation or compression along single or multiple axes, to define a desirable pattern density with overall reduced surface area, and to control the distribution and shaping from applied loads. The ability to mold, form or cut the struts 14 in a nearly endless array of sinusoidal or like configurations provides an implant 10 that can better tailor or mimic the anisotropic behaviors of physiological tissue.

One or more portions of the implant 10 can be constructed of a polymer coated, or impregnated or molded with a coloring. As such, the entire implant 10, or simply a portion of the implant such as the support portion 12, can be colored to stand out relative to the surrounding tissue. Coloring (e.g., blue) of the implant or implant portions can improve visualization and positioning of the implant 10 by the physician during implantation by providing desirable surface contrast. Further, various embodiments of the implant 10 can be constructed of opaque, or translucent, polymer materials.

Figure 3B:
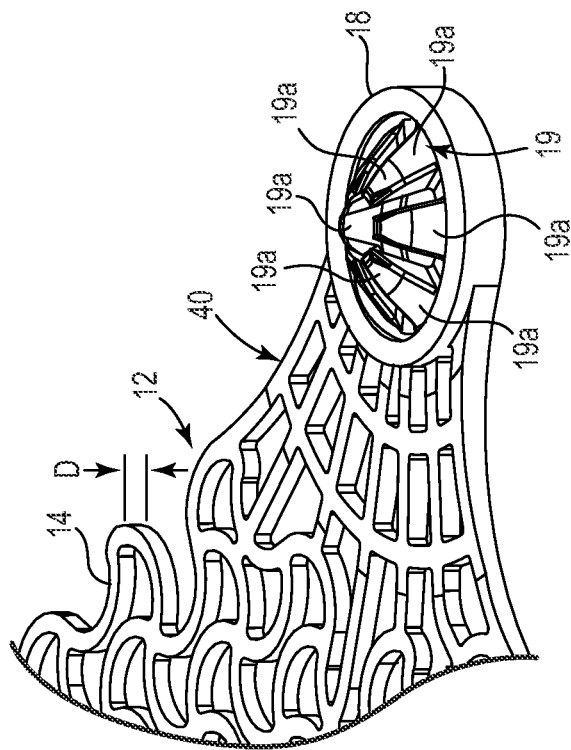
FIG. 3b is a partial close-up perspective view of an eyelet and support portion for a unitary patterned implant in accordance with embodiments of the present invention.
Figure 3A:
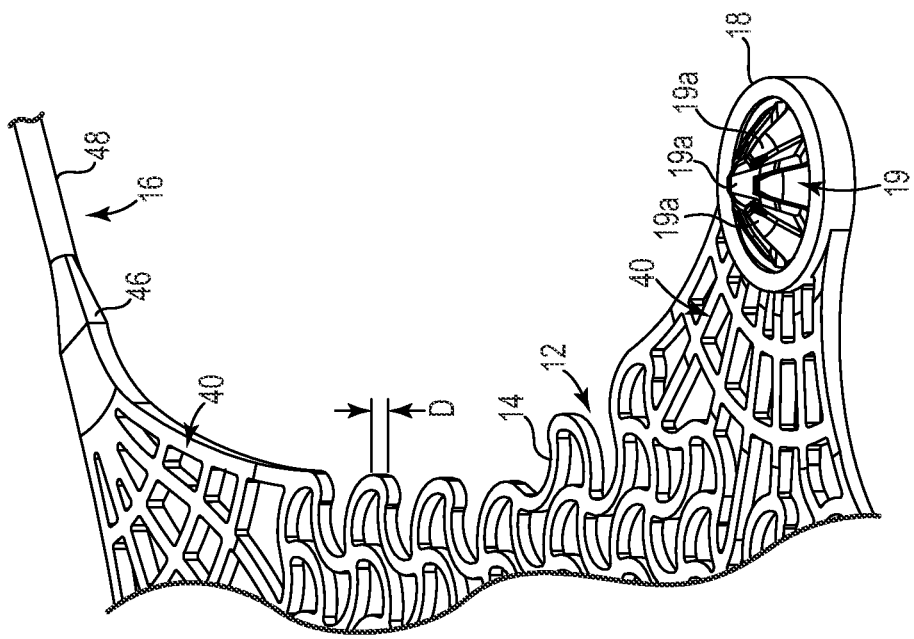
FIG. 3a is a partial close-up perspective view of an eyelet and support portion for a unitary patterned implant in accordance with embodiments of the present invention.
Figure 4:
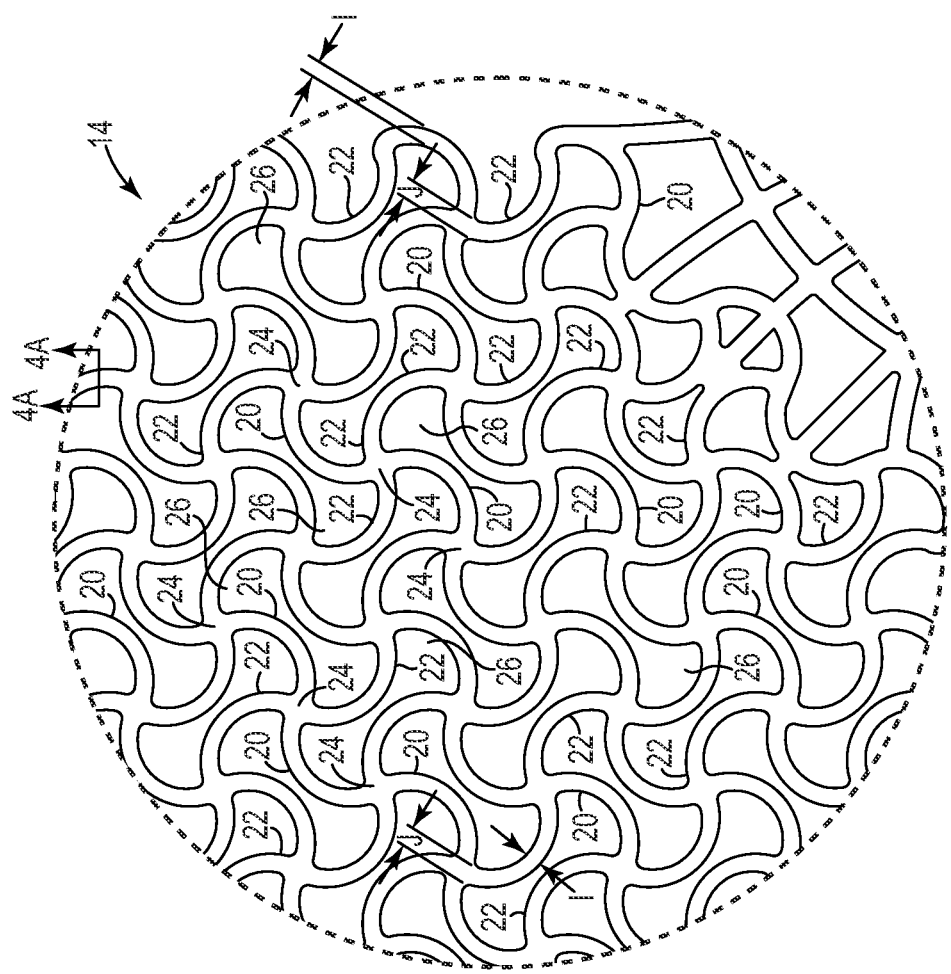
FIG. 4 is a partial close-up view of cellular patterns and structures for a unitary patterned implant in accordance with embodiments of the present invention.
Figure 6:
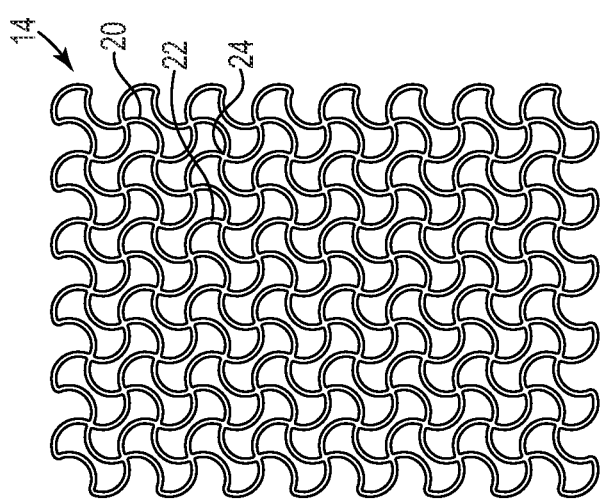
Figure 5:
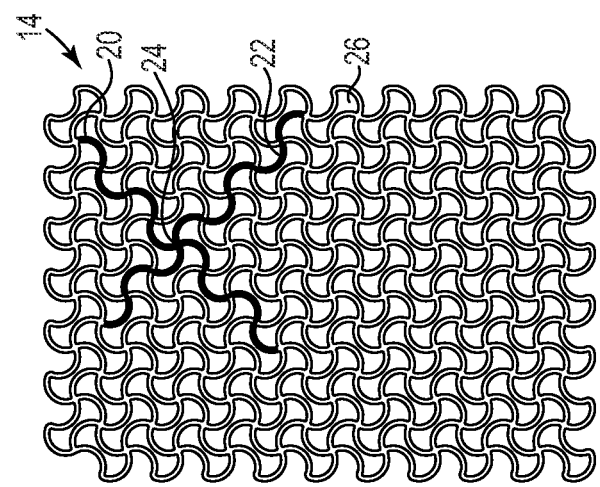

In certain embodiments, such as those depicted in FIGS. 1-6, the patterned struts 14 define a general pinwheel design including first angular strut lines 20 and second angular strut lines 22 crossing or intersecting at repeating fixed junctions 24 to define cellular voids 26. The thickness, size and separation of the struts 14 can be modified to create an implant 10 with different surface area and cellular density attributes. For instance, the implant 10 embodiment of FIG. 5 shows a relatively dense implant pattern, while FIG. 6 shows a less dense implant pattern.

Figure 7:
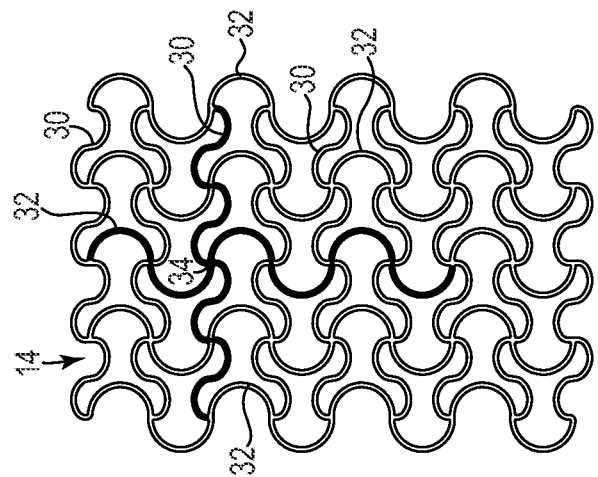
FIGS. 5-7 are partial views of cellular patterns and structures for unitary patterned implants in accordance with embodiments of the present invention.

The embodiment of FIG. 7 demonstrates an implant 10 constructed of patterned struts 14 including a first generally horizontal strut line 30 and a second generally vertical strut line 32 crossing or intersecting at repeating fixed junctions 34 to define cellular voids 36. Again, the thickness, size and separation of the struts 14 can be modified to create an implant 10 with different surface area and cellular density attributes.

As demonstrated in FIGS. 1-2, embodiments of the implant 10 can include a symmetry axis A. The Axis A can take on shapes and dimensions similar to that of the surrounding sinusoidal cell configurations. In addition to providing physical compression and support characteristics similar to the surrounding cells, the axis A can serve as an important marker or line of reference during implantation. As such, the axis A can be colored or otherwise marked to visually stand out relative to the implant 10 as a whole. In various embodiments, the axis A can be colored or marked along a length shorter than its entire length. Variations on the visual marking of the axis A are envisioned for embodiments of the present invention.

As shown in FIG. 4, the dimensional design of the implant struts 14 can be configured to promote targeted strength and flexibility. For instance, the material width J at the fixed junctions 24, 34 can be measurably greater than the material width I of the struts 14 intermediate the junctions to allow for increased strength at the junctions. Strengthened and widened junctions 24, 34 can handle and absorb greater stress or torque resulting from implant positioning, twisting and general manipulation. Conversely, thinner strut portions intermediate the junctions 24, 34 promote increased flexibility and controllability of the implant 10 during positioning and device manipulation. This flexibility will also provide an implant 10 adapted to properly conform to unique patient anatomy and lay flat against such anatomy to provide optimal support distribution, tissue in-growth and like characteristics. In one embodiment, the junctions 24, 34 can range in material size or width (J) from 0.017 inches to 0.020 inches. The intermediate strut portions 35 can range in material size or width (I) from 0.014 inches to 0.017 inches. Other dimensional ranges and proportions are envisioned for embodiments of the struts and strut portions depending on the particular application, strength, flexibility, stress distribution or other performance needs of the implant. In various embodiments, the general thickness or depth D of the struts 14 and implant construct ranges from 0.010 inches to 0.020 inches. Of course, the structures of the implant 10 can be provided in other sizes as well.

Additional benefits are presented with the homogenous non-woven design and targeted strength regions (e.g., fixed junctions) of the implant 10. Namely, a flexible but strong implant 10 is provided, while still maintaining a low surface area, lower inflammatory response, less scarring and increased density.

The patterned implant 10 also provides benefits over traditional knitted or woven mesh in the area of compression and the reaction to longitudinal extension strain. Traditional knitted or woven mesh implants can tend to compress and narrow during longitudinal stretching, thereby displaying a positive Poisson affect or ratio. Conversely, the sinusoidal cell and strut configurations of the patterned implants 10 of the present invention can display a Negative Poisson affect or ratio. In particular, as the implant 10 is loaded or stretched (e.g., at ends, anchors, corners or upon the planar surfaces), the strut and cell structures resist compression and measurably expand to provide a stable and generally planar surface area for tissue or organ support. The combination of the struts and fixed junctions facilitate this Negative Poisson affect.

Figure 4A:
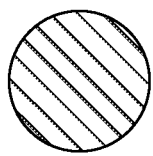
FIG. 4a is a cross-section schematic view of a strut member from FIG. 4.

As shown in FIGS. 4-4A, the cross section of the non-woven strut members 14 are generally circular with exemplary embodiments of the present invention. This is a significant advantage over the woven or knitted filament mesh stands of conventional implants. The circular cross-section of the struts 14 of the present invention provide a improved implantation feel and a consistent surface adapted to lay flat and retain its shape against target tissue, and to reduce or eliminate snagging or resistance during deployment and positioning.

Embodiments of the implant 10 can include one or more transition portions or zones 40, as shown particularly in FIGS. 1-3b. In general, the zones 40 provide a material transition between the cellular construct of the support portion 12 and anchoring or like features 16 of the implant 10, e.g., anchors, eyelets, etc. The transition zones 40 can take on various sizes, shapes and designs to provide increased strength and stress absorption/distribution for portions of the implant 10 being pulled, pushed and twisted during deployment and positioning of the implant 10. Embodiments of the zones 40 can include arcuate lattice or cell structures fanning out from or into the support portion 12 and the anchoring portions 16. The zones 40 can be tapered into or away from the support portion 12 or anchoring portion 16 to facilitate stress and tension distribution such that the struts 14 and cell structures of the support portion 12 are protected from tearing, ripping or other material breaches.

The structure and design of anchoring features of portions 16 of the implant 10 can vary greatly depending on the particular implantation and support needs of the particular device. In certain embodiments, the anchor portions 16 can include first and second anterior and opposing anchors 42, 44 extending out angulary from an anterior end region of the implant 10. A barrel 46 can extend out from the transition zone 40 to an anchor rod 48. A tissue anchor 50 is provided at a distal end of the anchor rod 48 such that the rod 48 extends intermediate the anchor 50 and barrel 46, or transition zone 40. The tissue anchor 50 can include one or more tines 51 adapted to engage and/or penetrate soft tissue, e.g., the obturator internus muscles. The anchor rod 48 can be generally cylindrical in certain embodiments (FIG. 1), or generally flat or rectangular in other embodiments (FIG. 2). The cylindrical anchor rod 48 is adapted to absorb and comply with twisting or other like motions imposed on the anchor portion 16 during deployment and positioning of the implant 10. While the anchor rod 48 is shown as being substantially linear (e.g., FIGS. 1-2), other embodiments of the anchor rod 48 can include kinks, curved sections, and like features to facilitate manipulation of the implant during deployment and to better engage and disengage with introducer tools and devices. Further, sections of the anchor portion 16, including the anchor rod 48, can be generally rigid, or flexible, depending on the particular strength and anchor displacement needs.

In addition to the anchors 50 and rods 48 depicted herein, other configurations are also envisioned. For instance, the anchor 50 can be rotatably or pivotably affixed to the rods 48, any other portion of the anchor portions 16, or the transition zones 40. Any of the anchors depicted or described herein can be integrally formed with a portion of the implant 10, or separately attachable or detachable therefrom.

The support portion 12 can include one or more eyelets 18, with transitioning zones 40 extending or spanning intermediate the eyelets 18 and the strut 14 cell structures. An aperture extends through each of the eyelets 18. The eyelets 18 can simply include corresponding apertures for engagement with anchoring members or devices, or the eyelets 18 can be integrally formed with a grommet 19 having a plurality of extending or angular teeth 19a. The teeth 19a are adapted to engage and retain various anchoring structures, such as anchor mesh, extensions, apertures or protruding members. The eyelets 18, and any corresponding material or structures associated with the eyelets 18, can be provided along any side, end or body portion of the implant 10, depending on the particular anatomical and treatment application. Moreover, a variety of sizes, quantity and shapes are envisioned for the eyelet 18 configurations for embodiments of the implant 10.

As shown in FIG. 3, a formed or cut component, such as the eyelet 18, can include one or more apertures adjacent the feature 18a to facilitate secondary molding operations allowing other polymer materials or components to locate and form a surface protection fused to the initial main body or support portion 12 without damaging the surrounding structure.

Referring again to FIGS. 1-2 generally, the implant 10 can include a posterior end region 15 adapted for implantable orientation at or proximate the posterior pelvic region. The end region 15 can be constructed to have varying lengths and shapes. In certain embodiments, the length of the end region 15 can extend out a length longer than that depicted in FIGS. 1-2. The anatomical dimensions of the patient, a desire to fold or later cut or remove a "tail" from the region 15, and other factors can dictate or influence the dimensions and proportions of the region 15.

Figure 10:
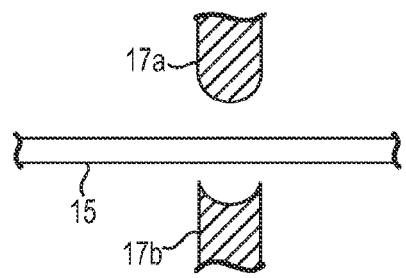
FIGS. 10-12 are close-up views of a weakening or marking method for use with a portion of a patterned implant in accordance with embodiments of the present invention.
Figure 11:
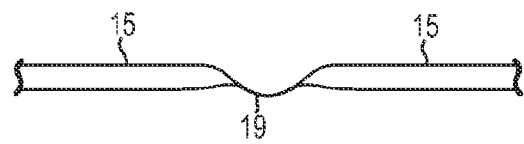
Figure 12:
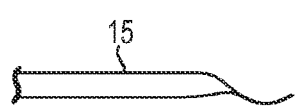

Various embodiments of the region 15 can include markings or indicia to indicate lines or sections of trimming, tearing or for cutting extra material from the region 15. In addition, scoring, indenting, crushing, weakening and like procedures or features can be included along one or more portions of the region 15 to indicate trimming lines or zones. FIGS. 10-12 show an exemplary method of crushing a trim line 19 along a length or portion of the struts or film of the region 15 with a crushing apparatus 17a, 17b to facilitate tearing, cutting or otherwise removing the excess tail material.

Various cutting tools can be employed as well to trim the tail or extra material from the implant 10. In one embodiment, a dull scissor-like device can crush and cut through the strut 14 materials along a designated or targeted line such that the crushing action pinches the struts to reduce or eliminate potentially sharp edges or protrusions in the materials remaining with the implant 10. Other cutting tools can include a heating feature to apply heat at the time of crushing or cutting to remove excess material away from the implant 10 to also reduce or eliminate potentially sharp edges.

Other embodiments can include a modular or expandable region 15, wherein one or more distinct sections of material can be added to the region 15 to extend the size or shape of the implant tail. The distinct material can be constructed as traditional filament mesh or as a unitary homogeneous structure in accordance with the configuration of the implant 10. These additional sections can be added via sutures, interlocking members (e.g., engaging bulbs/heads, or engaging hook and loop connectors, etc.), clips, snaps, fasteners, and like structures, features or techniques.

Figure 7A:
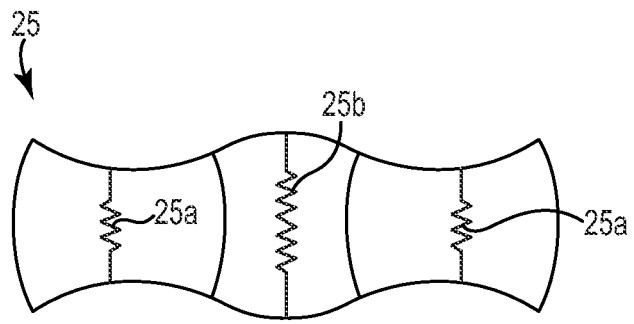
FIGS. 7a-7b are partial close-up views of cellular patterns and stretch elements for a unitary patterned implant in accordance with embodiments of the present invention.
Figure 7B:
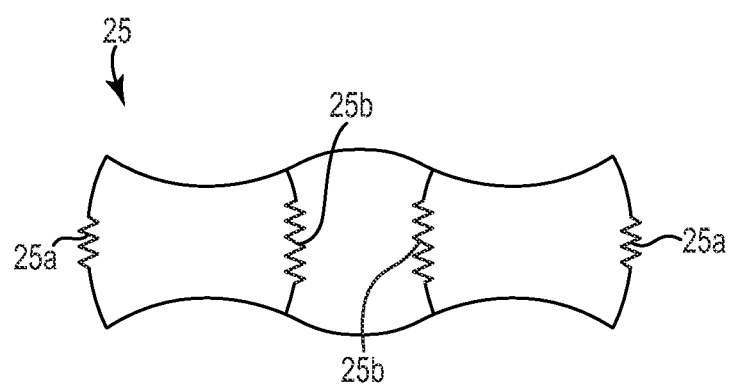

In still other embodiments, as demonstrated in FIGS. 7a-7b, the posterior region 15, or other portions of the implant 10, can include strut 14 geometry allowing for pulling and stretching of the struts 14 to deform and define a new shape or size for that particular region of the implant. For instance, one or more strut patterned sections of the implant 10 can include various sinusoidal stretch elements 25. Low frequency sinusoid struts 25a can be included at the outer portion of the designated pattern, while higher frequency sinusoid struts 25b can be included within the pattern. The lower frequency struts 25a can deform to hold a shape during stretching, while the higher frequency struts 25b exhibit partial to no plastic deformation, thereby becoming supporting or strength members for the stretched cell or pattern. The frequency, size and shape of the struts 25a, 25b can vary to provide a myriad of options for the stretch length and direction parameters. In one application, a portion, such as the region 15, can include these stretch elements 25 to permit selective stretching or expansion of at least a defined area of the region 15 to accommodate particular patient anatomy or implantation needs. The stretch elements and corresponding geometry can be provided in all or only selected cell patterns of the implant 10 to provide targeted stretchability or deformability sections.

Figure 9:
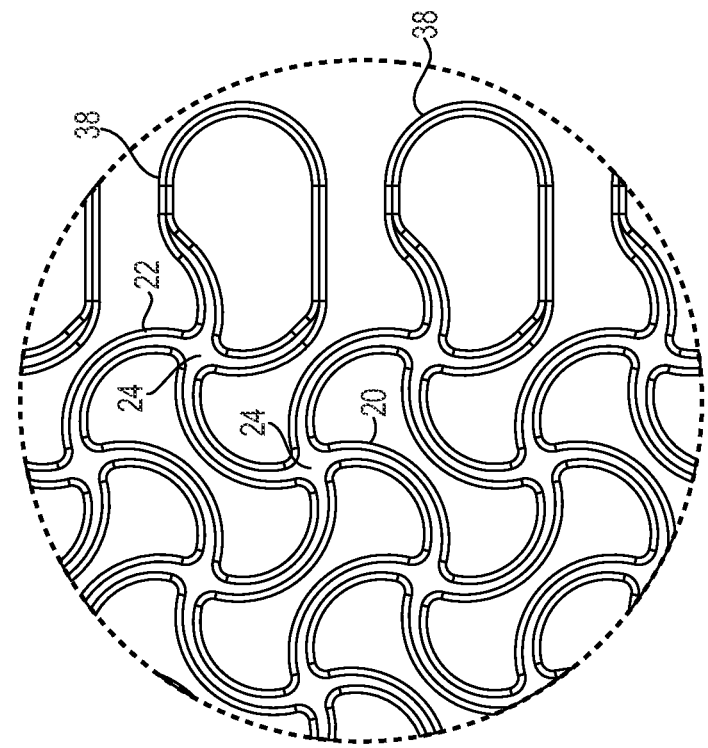
FIG. 9 is a close-up view of a portion of the cellular pattern and extending members from FIG. 8.
Figure 8:
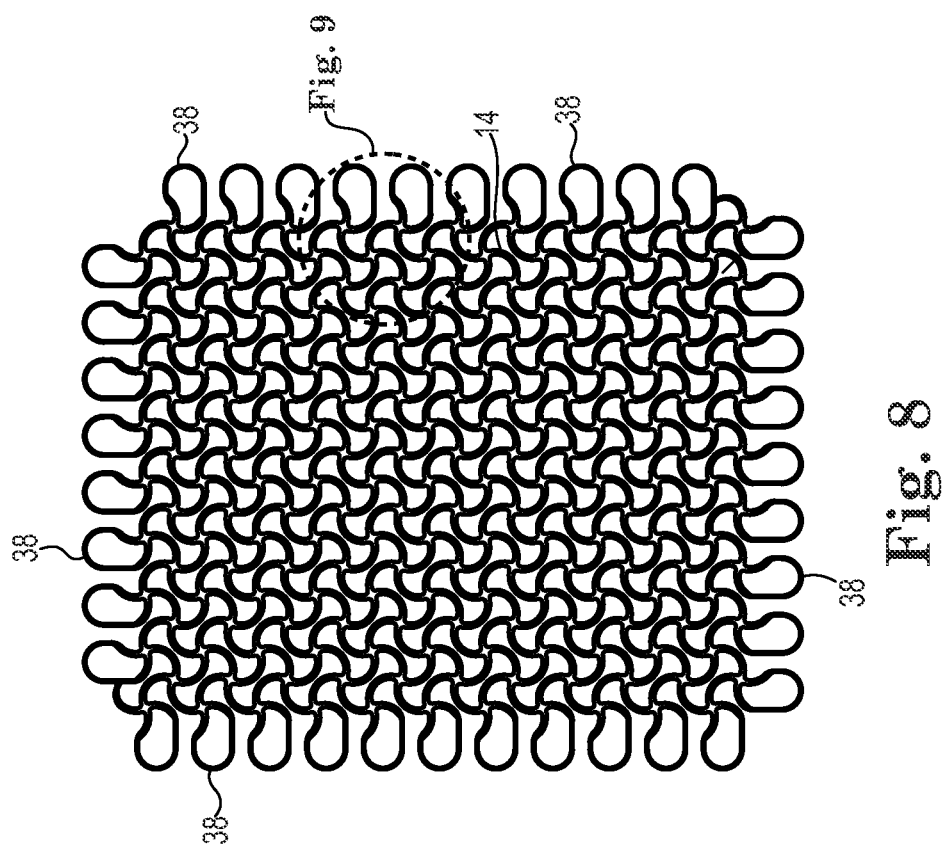
FIG. 8 is a partial view of a cellular pattern and extending members for a unitary patterned implant in accordance with embodiments of the present invention.

As shown in FIGS. 8-9, portions or edge regions of the implant 10 can include a plurality of spaced extending wisps or members 38. The members 38 can serve to soften the tactile feel and operative contact of the edges of the unitary implant 10. The members 38 can be integrally formed to extend from the struts 14. The members 38 can be configured as relatively flexible looped, linear or arcuate extensions. Certain embodiments of the members 38 can be provided with the implant 10 such that they remain substantially within or along the plane of the implant 10. Other embodiments can include members 38 adapted to measurably extend or displace transversely relative to the plane of the implant 10.

Figure 13:
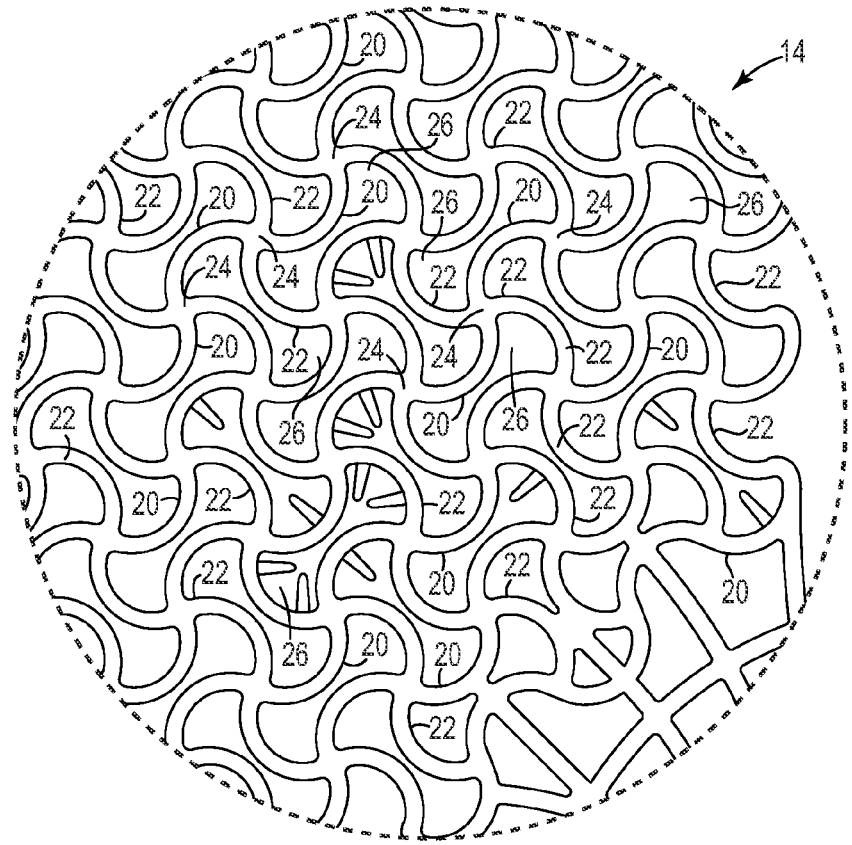
FIG. 13 is a partial close-up view of cellular patterns and void nub structures for a unitary patterned implant in accordance with embodiments of the present invention.
Figure 14:
FIG. 14 is a side view of an anchor or fixation arm for use in anchoring a portion of a unitary patterned implant in accordance with embodiments of the present invention.
Figure 15:
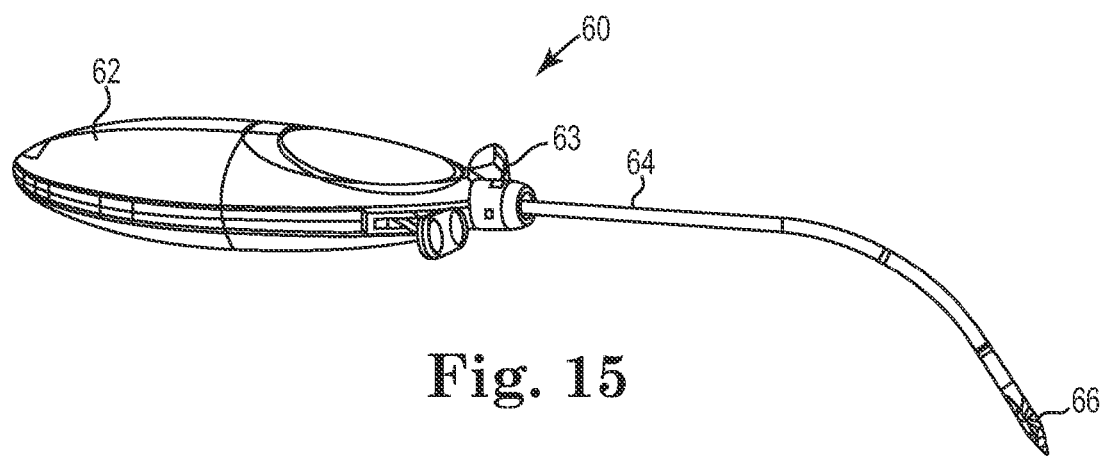
FIGS. 15-16 are views of insertion tools adapted for use to position and deploy a unitary patterned implant in accordance with embodiments of the present invention.
Figure 16:
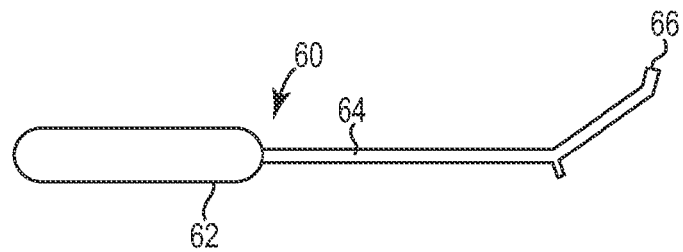

As shown in FIG. 13, the implant 10 support portion 12 can include a plurality of protuberances or nubs 25 generally extending and lying within the cell structure or strut 14 construct of the implant 10. One or more of the nubs 25 can be included within any, or all, of the defined cell voids 26. The nubs 25 can extend substantially along the same plane as the implant 10, or generally transverse to that plane. The nubs 25 can provide increased load support and contact points while not substantially increasing the surface area of the support portion 12 of the implant 10. In addition, the spacing and configuration of the nubs 25 still permits and promotes tissue in-growth within the voids 26.

The implants 10 described herein can be implanted into a patient by use of various different types of surgical tools, including insertion tools, which generally are tools useful to engage and place a tissue anchor or a connector that is secured to an extension portion of an implant. Various types of insertion tools are known, including those in the previously-incorporated references, and these types of tools and modifications thereof can be used according to the present description to install the implant 10.

Examples of various insertion techniques and tools are included in FIGS. 14-18. Each tool 60 can include a handle 62, needle 64 and engaging distal tip 66. The handle 62 can include an actuation mechanism 63 in operative communication with the distal tip 66 and adapted to selectively control engagement and/or disengagement of the distal tip 66 with portions of the implant 10 (e.g., anchors 50). In various embodiments, the distal tip 66 of a certain tool 60 is adapted to engage with, deploy, position and anchor or insert an anchor fixation arm 68 into the sacrospinous ligament of the patient, with a length or portion of the fixation arm 68 fed through and secured to the eyelet 18 and grommet 19 feature of the implant 10. The anchor fixation arm 68 can include a rod or extension 68a, a mesh portion 68b, and a distal anchor 68c. Certain embodiments of the anchor fixation arm 68 can include an external sheath adapted to shroud portions of the arm 68 during deployment (e.g., the mesh 68b and anchor 68c).

In one embodiment of the surgical procedure for implanting the implant 10 within a female patient to treat vaginal prolapse, an incision is made in the anterior vaginal wall of the patient, and a full thickness dissection is made of the anterior wall. Tissue is generally cleared from the sacrospinous ligaments. The tissue anchors 50 (adapted as anterior fixation anchors) are loaded on to the distal tip 66 of an anterior fixation tool 60. The tissue anchors 50 are then inserted into the obturator internus muscle with a finger-guided needle 60, bilaterally. The implant 10 can be trimmed and sutured to the anatomy as required. Next, the fixation arm 68 is loaded onto a corresponding needle tool 60, advanced through to the sacrospinous ligament and the distal anchor 68c of the arm 68 is inserted through the ligament to provide fixation. Again, an actuation mechanism 63 can be activated to disengage the arm 68 or its respective anchor 68c from the tool 60. In those embodiments of the arm 68 having an outer sheath or sleeve, the sleeve can be removed. Alternatively, the sheath can remain in place to provide bidirectional adjustment of the arm 68 within the eyelet/grommet aperture configuration of the implant 10. Again, this ligament fixation can occur bilaterally.

Once the arms 68 are fixated within the target ligaments (on each side), the eyelet 18 and grommet 19 on each side of the implant 10 is slid over and along the respective arm 68 (e.g., rod 68a and mesh 68b portions). As such, the grommet teeth 19a will grab onto and secure the mesh 68b of the fixation arm 68 therein. Final tension and adjustment can be provided at the fixation and related portions of the implant 10. Next, excess lengths of the fixation arms 68 extending out from the eyelet 18 can be trimmed and removed. The vaginal incision can then be closed with sutures to complete the procedure.

Figure 17:
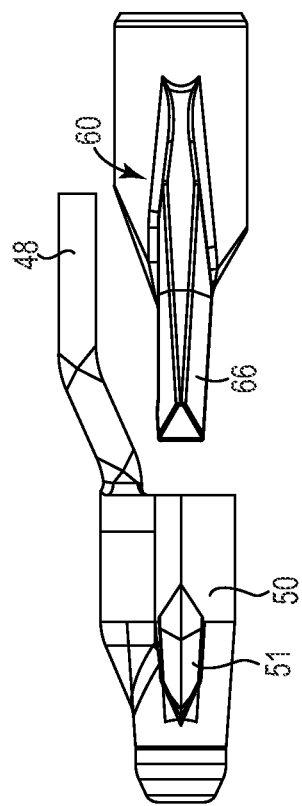
FIGS. 17-18 are side views of anchor and insertion tool portions for use to position and deploy a unitary patterned implant in accordance with embodiments of the present invention.
Figure 18:
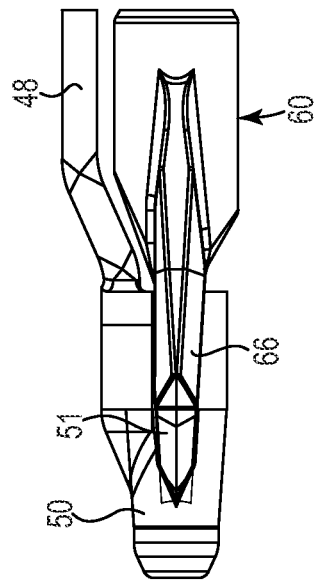
Figure 19:
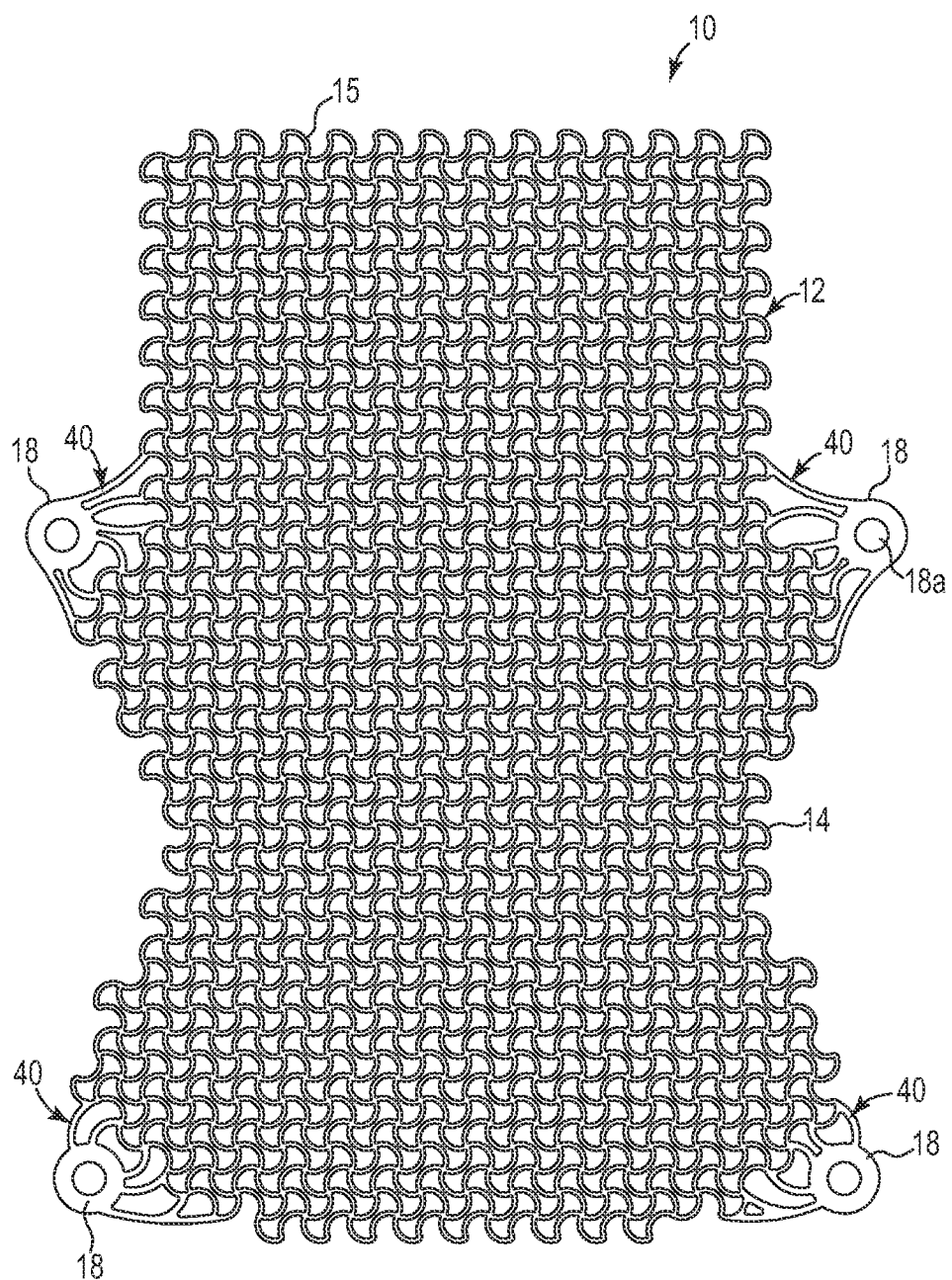
Figure 20:
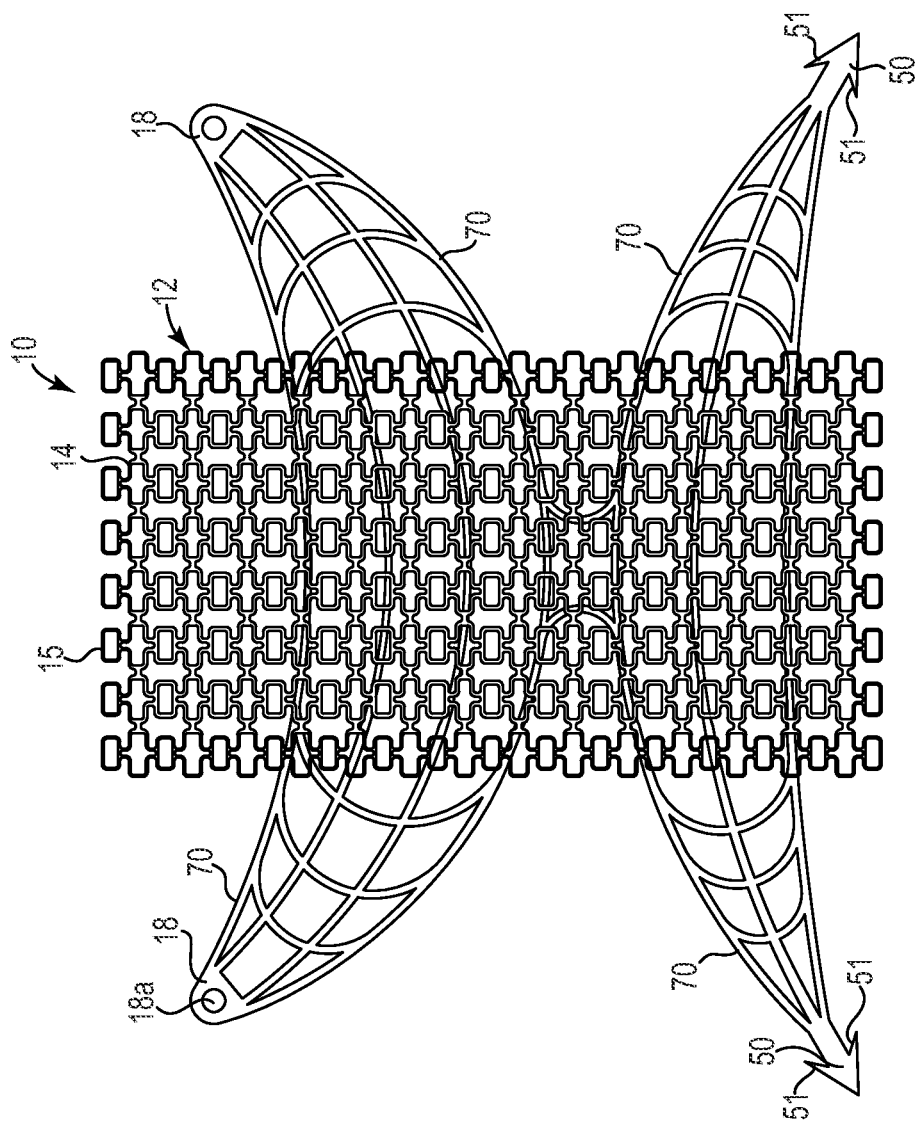

To facilitate proper deployment of the anchor 50 from the needle 60 and into target tissue (e.g., obturator internus muscle), the rod 48 can be shaped or sized to better run along the tool 60 (FIGS. 17-18). Further, the rod 48 can include bends, kinks, twists or like features such that the anchor 50 is under torque (e.g., stored energy) when engaged at the end 66 of the tool 60. As such, once the anchor 50 is penetrated through the target tissue and disengaged from the end 66, the anchor will untwist or return to its original orientation (e.g, spring-like return), such that the anchor tines 51 align along a different plane or path from where they entered the target tissue. This realignment of the tines 51 post-fixation keeps the tines 51 from existing back through the tissue path created with the original tissue engagement or penetration. Other devices or methods can be employed to cause this post-penetration rotation or realignment of the anchor 50 and tines 51. For instance, a portion of the tool 60 (e.g., distal end 66) can be actuated to provide the desired rotation or realignment, or the tool 60 can be manipulated to cause the realignment. Further, the distal tip 66 of the tool 60 can be angled or positioned such that the anchor 50 is angled or askew during deployment, but then unleashed to a new alignment angle after release or disengagement from the tool 60.

FIGS. 19-22 demonstrate additional exemplary implant 10 designs, as well as cell and strut 14 patterns for use with embodiments of the invention. However, one of ordinary skill in the art will understand that a myriad of other shapes, sizes and configurations can be employed based on the teachings provided herein. Further, the implant 10 and support portion 12 can be constructed and sized to serve as an elongate incontinence sling, or as a larger prolapse implant.

The implant 10 can include extending arms 70 providing load distribution and/or anchoring features. The support portion 12 can be integrally formed with the arms 70, or separately fused together to form a unitary body. As with the various embodiments of the present invention, the struts 14 can have variable widths or thicknesses, can be tapered, can include apertures, or can include defined shapes and/or patterns, e.g., sinusoids, squares, elliptical, triangular, elbowed, straight, or other simple or complex shapes and patterns. Unique strut 14 designs and cellular patterns can be included within a single implant 10 to provide different zones, having different stress, load distribution or compression characteristics. Other strut 14 designs and patterns can be employed as well to achieve the functionality described and depicted herein.

By arranging the density of the cell patterns with the embodiments of the implants 10 of the present invention, it is possible to tailor the elongation, load or strength properties of the implant 10 according to specific needs and support requirements. Moreover, more than one material can be used to construct the implant 10 to further control desired load and stress properties, e.g., combining different polymers such as polypropylene, PEEK, PET, PTFE, PGA, PLA, etc. Polymers could also be combined with metallic elements to alter strength and elongation profiles of the implant 10. The stronger materials would take up stresses from higher load regions faster, thereby allowing for a method to selectively control performance characteristics of the implant 10. Moreover, a polymer or metal frame could be provided along the periphery or other select areas of the implant 10 to provide additional strength or rigidity properties.

As detailed herein, various structures and components of the present invention can be integrally formed into a unitary body via a molding process. For instance, an injection molding machine (e.g., Milacron Roboshot S2000i 33B machine) having internal vacuum and cooling lines can be employed. In general, a dry resin, such as a polypropylene resin (e.g., Pro-fax PD 626), is maintained at approximately 170° F. for several hours. In addition, the mold device can be heated to approximately 130° F. Then, the mold vacuum lines can be started and the injection molding cycle initiated. The mold cavities will be filled and the device will be cooled for a period of time (e.g., 18 seconds). Upon completion, the mold is opened and part ejection will activate with evacuation. The mold can then be closed and the cycle repeated for additional injection molded implants. Other known molding processes and systems can be employed with the present invention as well.

Embodiments of the implant 10 can be formed or cut along a precise cutting tool path (e.g., using the DPSS 266 laser system), to cut the implant 10 and strut 14 features and designs in an already unitary film or sheet of polymer material. Alternatively, the implant features and portions can be stamped into such a unitary film or sheet material.

The implants 10, their various components, structures, features, materials and methods may have a number of suitable configurations and applications, as shown and described in the previously-incorporated references. Various methods and tools for introducing, deploying, anchoring and manipulating implants to treat incontinence and prolapse as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A unitary patterned implant device for treating vaginal prolapse in a patient, comprising:

a non-woven unitary support portion including a plurality of undulating strut members joined at and spanning out from a plurality of fixed junctions to define a plurality of substantially identical repeating cells having voids, the support portion having first and second opposing eyelets;

first and second opposing anchor portions provided a distance from the first and second opposing eyelets, with each of the first and second opposing anchor portions further including a cylindrical rod extending out from the anchor portions and a tissue anchor provided at a distal end of the cylindrical rod of each of the first and second opposing anchor portions, the tissue anchor having one or more angled tines and an anchor length;

at least one transition zone integrally formed with the support portion and the first anchor portion, defining a plurality of generally elongate non-woven cells of a different shape and larger than the substantially identical repeating cells of the support portion, and spanning between the support portion and the first anchor portion such that the at least one transition zone tapers and narrows from the support portion to the first anchor portion; and an anchoring arm having a distal tissue anchor and an extending rod member adapted to slidably engage and secure with one of the first and second eyelets of the support portion.

2. The implant device of claim 1, further including a grommet having a plurality of extending teeth, the grommet integrally formed with at least one of the first and second opposing eyelets.

3. The implant device of claim 1, further including a central axis line defined in the plurality of undulating strut members.

4. The implant device of claim 1, further including a removable posterior tail portion.

5. The implant device of claim 4, wherein the removable posterior tail portion includes a crush line along a portion of the undulating strut members.

6. The implant device of claim 1, further including stretch sinusoid elements with a plurality of the plurality of undulating strut members to provide selective stretching of a portion of the support portion.

7. The implant device of claim 6, wherein the stretch sinusoid elements includes at least one low frequency sinusoid element and at least one high frequency sinusoid element.

8. The implant device of claim 1, further including a plurality of nubs disposed and extending within a plurality of the voids.

9. The implant device of claim 1, further including a second transition zone spanning between the non-woven unitary support portion and the second anchor portion.

10. The implant device of claim 1, wherein a plurality of the repeating cells display a Negative Poisson ratio during a load application.

11. A unitary implant system for treating vaginal prolapse in a patient, comprising:

a non-woven unitary support portion including a plurality of undulating strut members joined at and spanning out from a plurality of fixed junctions to define a plurality of substantially identical repeating cells having voids, the support portion having first and second opposing eyelets and first and second opposing anchor portions provided a distance from the first and second opposing eyelets and extending out from the support portion with each of the first and second opposing anchor portions further including an end anchor and a cylindrical anchor rod;

a transition zone integrally formed with the support portion and the first anchor portion, defining a plurality of generally elongate non-woven cells of a different shape and larger than the substantially identical repeating cells of the support portion, and spanning between the support portion and the first anchor portion such that the transition zone tapers and narrows from the support portion to the first anchor portion;

an insertion tool having a handle, a needle and a distal tip; and an anchoring arm having a distal tissue anchor and an extending rod member, wherein the distal tissue anchor is adapted to releasably engage with the distal tip of the insertion tool and the extending rod member is adapted to slidably engage and secure with one of the first and second eyelets of the support portion.

12. The system of claim 11, further including a grommet having a plurality of extending teeth, the grommet integrally formed with at least one of the first and second opposing eyelets.

13. The system of claim 12, wherein the anchoring arm further includes a mesh element securable within the plurality of extending teeth of the grommet.

14. The system of claim 11, wherein the support portion further includes a removable posterior tail portion.

15. The system of claim 14, wherein the removable posterior tail portion includes a crush line along a portion of the undulating strut members.

16. The system of claim 11, wherein the support portion further includes stretch sinusoid elements with a plurality of the plurality of undulating strut members to provide selective stretching of a portion of the support portion.

17. The system of claim 11, further including a plurality of nubs disposed and extending within a plurality of the voids.

18. The system of claim 11, wherein a plurality of the repeating cells display a Negative Poisson ratio during a load application.

19. The system of claim 11, wherein the insertion tool further includes an actuation mechanism in operative communication with the distal tip and adapted to releasably engage the distal tissue anchor from the distal tip.

20. The system of claim 11, wherein the unitary support portion is formed from a polymer molding process.

* * * * *